US008884079B2

(12) United States Patent
Jevtic et al.

(10) Patent No.: US 8,884,079 B2
(45) Date of Patent: Nov. 11, 2014

(54) REDUCING IMPURITIES IN HYDROGENATION PROCESSES WITH MULTIPLE REACTION ZONES

(75) Inventors: Radmila Jevtic, Pasadena, TX (US); Victor J. Johnston, Houston, TX (US); R. Jay Warner, Houston, TX (US); Dheeraj Kumar, Pearland, TX (US); Heiko Weiner, Pasadena, TX (US)

(73) Assignee: Celanese International Corporation, Dallas, TX (US)

( * ) Notice: Subject to any disclaimer, the term of this patent is extended or adjusted under 35 U.S.C. 154(b) by 591 days.

(21) Appl. No.: 13/197,700

(22) Filed: Aug. 3, 2011

(65) Prior Publication Data

US 2013/0035520 A1 Feb. 7, 2013

(51) Int. Cl.
*C07C 27/04* (2006.01)
*C07C 29/88* (2006.01)
*C07C 29/149* (2006.01)

(52) U.S. Cl.
CPC ............... *C07C 29/149* (2013.01); *C07C 29/88* (2013.01)
USPC .......................................... 568/885; 568/884

(58) Field of Classification Search
CPC ............................ C07C 29/147; C07C 29/149
USPC .................................................. 568/884, 885
See application file for complete search history.

(56) References Cited

U.S. PATENT DOCUMENTS

| | | |
|---|---|---|
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,990,952 A | 11/1976 | Katzen et al. |
| 4,275,228 A | 6/1981 | Gruffaz et al. |
| 4,306,942 A | 12/1981 | Brush et al. |
| 4,319,058 A | 3/1982 | Kulprathipanja et al. |
| 4,379,028 A | 4/1983 | Berg et al. |
| 4,398,039 A | 8/1983 | Pesa et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,569,726 A | 2/1986 | Berg et al. |
| 4,626,321 A | 12/1986 | Grethlein et al. |
| 4,678,543 A | 7/1987 | Houben et al. |
| 4,692,218 A | 9/1987 | Houben et al. |
| 4,842,693 A | 6/1989 | Wheldon |
| 4,886,905 A | 12/1989 | Larkins, et al. |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,250,271 A | 10/1993 | Horizoe et al. |
| 5,254,758 A | 10/1993 | Hiles et al. |
| 5,362,918 A | 11/1994 | Aizawa et al. |
| 5,449,440 A | 9/1995 | Rescalli et al. |
| 5,502,248 A | 3/1996 | Funk et al. |
| 5,527,969 A | 6/1996 | Kaufhold et al. |
| RE35,377 E | 11/1996 | Steinberg et al. |
| 5,599,976 A | 2/1997 | Scates et al. |
| 5,770,770 A | 6/1998 | Kim et al. |
| 5,821,111 A | 10/1998 | Grady et al. |
| 5,861,530 A | 1/1999 | Atkins et al. |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,143,930 A | 11/2000 | Singh et al. |
| 6,232,352 B1 | 5/2001 | Vidalin et al. |
| 6,375,807 B1 | 4/2002 | Nieuwoudt et al. |
| 6,472,555 B2 | 10/2002 | Choudary et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |

(Continued)

FOREIGN PATENT DOCUMENTS

| | | |
|---|---|---|
| EP | 0104197 | 4/1984 |
| EP | 0167300 | 1/1986 |
| EP | 0400904 | 5/1990 |
| EP | 0372847 | 6/1990 |
| EP | 0456647 | 11/1991 |
| EP | 2060553 | 5/2009 |
| EP | 2060555 | 5/2009 |
| EP | 2072487 | 6/2009 |
| WO | WO 83/03409 | 10/1983 |
| WO | WO 90/07367 | 7/1990 |
| WO | WO 2009/063176 | 5/2009 |
| WO | WO 2009/105860 | 9/2009 |
| WO | WO 2010/055285 | 5/2010 |
| WO | WO 2011/097219 | 8/2011 |

OTHER PUBLICATIONS

International Search Report and Written Opinion for PCT/US2011/046484 mailed Oct. 5, 2012.

(Continued)

*Primary Examiner* — Sudhakar Katakam

(57) ABSTRACT

In a hydrogenation processes, a second lower temperature hydrogenation reactor is used to control the concentration of impurities, namely ethyl acetate, acetaldehyde, and acetal, prior to separating the reaction mixtures. Controlling impurities reduces the need for separation capital and improves overall efficiencies for recovering alcohols.

18 Claims, 5 Drawing Sheets

(56) References Cited

U.S. PATENT DOCUMENTS

| | | |
|---|---|---|
| 6,693,213 B1 | 2/2004 | Kolena et al. |
| 6,723,886 B2 | 4/2004 | Allison et al. |
| 6,765,110 B2 | 7/2004 | Warner et al. |
| 6,768,021 B2 | 7/2004 | Horan et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,115,772 B2 | 10/2006 | Picard et al. |
| 7,208,624 B2 | 4/2007 | Scates et al. |
| 7,297,236 B1 | 11/2007 | Vander Griend, et al. |
| 7,351,559 B2 | 4/2008 | Verser et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,863,489 B2 | 1/2011 | Johnston et al. |
| 7,884,253 B2 | 2/2011 | Stites et al. |
| 7,888,082 B2 | 2/2011 | Verser et al. |
| 8,502,001 B2 * | 8/2013 | Daniel et al. .................. 568/885 |
| 2003/0013908 A1 | 1/2003 | Horan et al. |
| 2006/0019360 A1 | 1/2006 | Verser et al. |
| 2006/0127999 A1 | 6/2006 | Verser et al. |
| 2007/0106246 A1 | 5/2007 | Modesitt |
| 2007/0270511 A1 | 11/2007 | Melnichuk et al. |
| 2008/0135396 A1 | 6/2008 | Blum |
| 2008/0193989 A1 | 8/2008 | Verser et al. |
| 2009/0005588 A1 | 1/2009 | Hassan et al. |
| 2009/0023192 A1 | 1/2009 | Verser et al. |
| 2009/0069609 A1 | 3/2009 | Kharas et al. |
| 2009/0281354 A1 | 11/2009 | Mariansky et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0137630 A1 | 6/2010 | Garton et al. |
| 2010/0197485 A1 | 8/2010 | Johnston et al. |
| 2011/0082322 A1 | 4/2011 | Jevtic et al. |

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

International Preliminary Report on Patentability for PCT/US2011/046484 mailed Feb. 13, 2014.

* cited by examiner

REDUCING IMPURITIES IN HYDROGENATION PROCESSES WITH MULTIPLE REACTION ZONES

FIELD OF THE INVENTION

The present invention relates generally to hydrogenation processes for producing ethanol and, in particular, to processes for purifying a crude ethanol product from the hydrogenation of alkanoic acid, such as acetic acid, and/or ethyl acetate by selective reaction of impurities.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

WO2009063176 describes a process for the conversion of acetic acid into ethanol involving introducing acetic acid and hydrogen into a primary hydrogenation unit and reacting to produce ethanol and ethyl acetate, introducing the ethyl acetate created with hydrogen into a secondary hydrogenation unit and reacting to produce ethanol, and recovering the ethanol.

U.S. Pat. No. 6,632,330 describes a process for the recovery of substantially pure alkyl alkanoate, such as ethyl acetate, from an impure feedstock. The impure feedstock is contacted with a selective hydrogenation catalyst in the presence of hydrogen in a selective hydrogenation zone maintained under selective hydrogenation conditions effective for selective hydrogenation of impurities containing reactive carbonyl groups thereby to hydrogenate the impurities to the corresponding alcohols. After recovery from the selective hydrogenation zone of a selectively hydrogenated reaction product mixture including the alkyl alkanoate and the corresponding alcohols, this is distilled in one or more distillation zones so as to produce substantially pure alkyl alkanoate therefrom which is recovered.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol comprising hydrogenating alkanoic acid in a first reaction zone operated at a first temperature to form a first reaction mixture comprising ethanol and one or more impurities. The impurities may be selected from the group consisting of ethyl acetate, acetaldehyde, acetal, and mixtures thereof. The process further comprises reacting at least a portion of the one or more impurities in a second reaction zone operated at a second temperature to form a second reaction mixture, and recovering ethanol from the second reaction mixture. Preferably at least one concentration of the impurities is reduced in the second reaction mixture. The second temperature is less than the first temperature, and preferably, the first temperature is from 125° C. to 350° C., and the second temperature is from 50° C. to 225° C.

In a second embodiment, the present invention is directed to a process for providing a first reaction mixture comprising ethanol, hydrogen, alkanoic acid, and from 0.1 wt. % to 10 wt. % acetal, acetaldehyde, and mixtures thereof and reacting the first reaction mixture in a reaction zone operated at a temperature from 50° C. to 225° C. to form a second reaction mixture having less than 1 wt. % acetal, acetaldehyde, and mixtures thereof. Preferably, the second reaction mixture may have from 0.0001 to 1 wt. % acetal, acetaldehyde, and mixtures thereof.

In a third embodiment, the present invention is directed to a process for producing ethanol comprising hydrogenating ethyl acetate, alkanoic acid, or mixture thereof in a first reaction zone operated at a first temperature to form a first reaction mixture comprising ethanol and one or more impurities. Ethyl acetate may be hydrogenated alone or with a mixture of ethyl acetate and acetic acid. The impurities may be selected from the group consisting of ethyl acetate, acetaldehyde, acetal, and mixtures thereof. The process further comprises reacting at least a portion of the one or more impurities in a second reaction zone operated at a second temperature to form a second reaction mixture, and recovering ethanol from the second reaction mixture.

In a fourth embodiment, the present invention is directed to a process for producing ethanol comprising hydrogenating ethyl acetate, alkanoic acid, or a mixture in a first reaction zone to form a first reaction mixture comprising ethanol and one or more impurities selected from the group consisting of ethyl acetate, acetaldehyde, and acetal, reacting at least one of the one or more impurities in a second reaction zone to form a second reaction mixture, wherein the concentration of the at least one of the one or more impurities in the second reaction mixture is less than the concentration the at least one of the one or more impurities in the first reaction mixture, and recovering ethanol from the second reaction mixture.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1A:
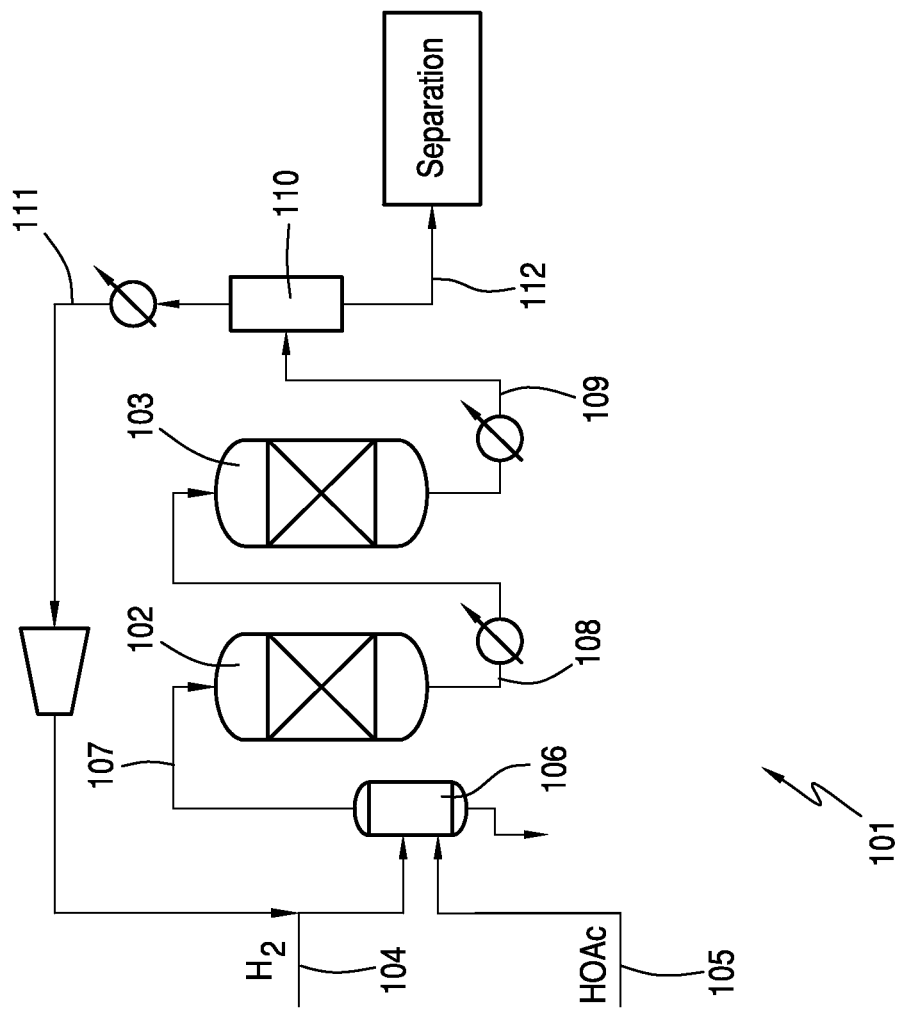
FIG. 1A is a schematic diagram of a hydrogenation reaction zone having dual reactors in accordance with one embodiment of the present invention.

The present invention relates to processes for recovering ethanol produced by hydrogenating an alkanoic acid, such as acetic acid, and/or ethyl acetate in the presence of a catalyst. The hydrogenation reaction of acetic acid produces a crude ethanol product that comprises ethanol, water, acetic acid, and impurities. The hydrogenation reaction of ethyl acetate and/or acetic acid produces a crude ethanol product that comprises ethanol, impurities, and optionally water and/or acetic acid. The impurities include compounds selected from the group consisting of acetaldehyde, acetals, ethyl acetate, and mixtures thereof. Various ethanol applications, such as industrial or fuel applications, require that these impurities be reduced to acceptable levels. To recover ethanol, these impurities, along with water and acetic acid, may be removed using a separation system containing distillation columns, adsorption units, membranes, and combinations thereof. However, even with separation systems it may be difficult to achieve low level of impurities required for some ethanol applications. Exacerbating the problem is the fact that some impurities may be formed during the separation process. The present invention, in some embodiments, advantageously provides a process for reducing impurities without using a complex separation system.

In one embodiment of the present invention, the concentration of impurities is reduced by using a low temperature hydrogenation process to selectivity reduce the concentration of impurities in the crude ethanol product. Preferably, the low temperature hydrogenation process is conducted prior to separating the crude ethanol product. In one aspect, the process of the present invention includes the step of hydrogenating acetic acid in a first reaction zone at a first temperature to produce a first reaction mixture comprising ethanol and one or more impurities. The first reaction mixture is fed to a second reaction zone that is operated at a second temperature less than the first temperature. In the second reaction zone, the total amount of the one or more impurities is reduced. Thus, the need for separating the impurities from the crude ethanol product is reduced and the efficiency of recovering ethanol may be improved. Additionally, the ethanol product recovered using embodiments of the present invention may have a low concentration of impurities.

The hydrogenation of acetic acid to produce ethanol, e.g., in the first reaction zone, is typically conducted in a reaction zone at elevated temperatures from 125° C. to 350° C., e.g., from 200° C. to 325° C., from 225° C. to 300° C., or from 250° C. to 300° C. The pressure in this reaction zone may range from 10 kPa to 3000 kPa, e.g., from 50 kPa to 2300 kPa, or from 100 kPa to 1500 kPa. The reactants may be fed to this reaction zone at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$. However, under these conditions impurities are formed along with the ethanol in the first reaction zone. The formation of impurities decreases overall ethanol yield and increases the energy required for ethanol separation.

The hydrogenation of acetic acid forms equal moles of ethanol and water. When all of the acetic acid is theoretically converted to ethanol and water, the resulting composition of the crude ethanol product would comprise 72 wt. % ethanol and 28 wt. % water. However, acetic acid conversion and selectivity to ethanol is typically less than 100%. Ethyl acetate may be formed from direct hydrogenation of acetic acid or by esterifying acetic and ethanol. Acetaldehyde, for example, is commonly formed as a byproduct in the hydrogenation of acetic acid to ethanol, and incomplete hydrogenation may result in a build up acetaldehyde as an impurity. In addition, acetaldehyde may react with several other compounds in the reactor, including ethanol, to form additional impurities. In particular, diethyl acetal (DEA) may be formed as an impurity during the hydrogenation of acetic acid. The formation of acetaldehyde, DEA or other acetals consumes the desired ethanol product, leading to decreased efficiency in recovering ethanol from the crude ethanol product. DEA and acetaldehyde may also be difficult to separate from the desired ethanol product. Other acetals may also be formed, including, ethyl propyl acetal, ethyl butyl acetal, dimethyl acetal, methyl ethyl acetal, and hemiacetals and mixtures thereof. Thus, it is desirable to reduce or remove ethyl acetate, acetaldehyde, and/or acetals from the crude ethanol product.

It has now been unexpectedly discovered that by further processing the crude ethanol product in a second hydrogenating reaction zone operated at a lower temperature than the first or primary reaction zone, the concentrations of at least one of ethyl acetate, acetaldehyde and/or acetal in the crude ethanol product can be reduced. In one embodiment, the first reaction mixture from the first hydrogenation reaction zone is introduced to a second hydrogenation reaction zone that is operated at a temperature less than the first reaction zone. Preferably, the second hydrogenation reaction zone is operated at a temperature from 50° C. to 225° C., e.g., from 100° C. to 160° C. or from 120° C. to 150° C., to form a second reaction mixture, e.g., an ethanol product. Depending on the first reactor temperature, the second reactor temperature may be at least 10% less, e.g., at least 25% less or at least 35% less. The second hydrogenation reaction zone may be operated at a temperature that is at least 20° C. less than first hydrogenation reaction zone, e.g., at least 50° C. less or at least 100° C. less. The second reaction mixture may undergo further processing or purification to recover ethanol.

Figure 1B:
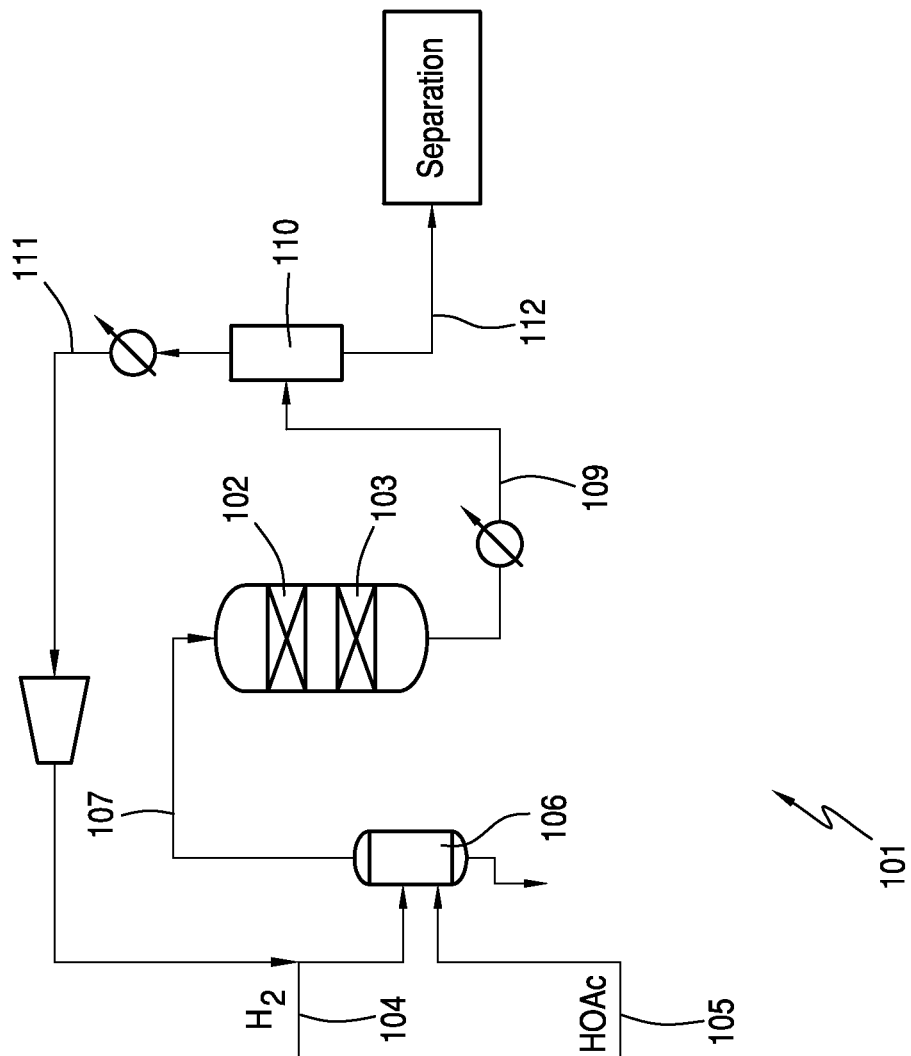
FIG. 1B is a schematic diagram of a hydrogenation reaction zone having a reactor with dual zones in accordance with one embodiment of the present invention.

The concentration of impurities, and in particular at least one of ethyl acetate, acetaldehyde, acetals and mixtures thereof, may be reduced in the second hydrogenation reaction zone. FIGS. 1A and 1B show systems having a first hydrogenation reaction zone and a second hydrogenation reaction zone. In FIG. 1A, the reaction zones are in separate vessels and separated by a heat exchanger for condensing the first reaction mixture. In FIG. 1B the reaction zones are contained in a common vessel and the two zones are operated at different temperatures. It should be understood that each reaction zone may contain multiple reactor beds.

In FIGS. 1A and 1B, hydrogenation reaction zone 101 comprises a first reaction zone 102 and a second reaction zone 103. Hydrogen and acetic acid via lines 104 and 105, respectively, are fed to a vaporizer 106 to create a vapor feed stream in line 107 that is directed to first reaction zone 102. In some optional embodiment, hydrogen and ethyl acetate may be fed to vaporizer. In one embodiment, lines 104 and 105 may be combined and jointly fed to the vaporizer 106. The temperature of the vapor feed stream in line 107 is preferably from 100° C. to 350° C., e.g., from 120° C. to 310° C. or from 150° C. to 300° C. Any feed that is not vaporized is removed from vaporizer 106 and may be recycled or discarded. In addition, although line 107 is shown as being directed to the top of first reaction zone 102, line 107 may be directed to the side, upper portion, or bottom of first reaction zone 102.

First reaction zone 102 contains the catalyst that is used in the hydrogenation of the alkanoic acid, preferably acetic acid, and/or ester, preferably ethyl acetate. In one embodiment, one or more guard beds (not shown) may be used upstream of first reaction zone 102, optionally upstream of the vaporizer 106, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. In FIG. 1A, during the hydrogenation process, a first reaction mixture is withdrawn, preferably continuously, from first reaction zone 102 via line 108. In FIG. 1B first reaction zone 102 and second reaction zone 103 are in the same vessel and the reaction mixture passes between zones in the vessel.

Prior to any separation, in FIG. 1A first reaction mixture in line 108, is fed to a second reaction zone 103. For purposes of the present invention, the first reaction mixture in line 108 should contain some amount of impurities, e.g., a total concentration of acetaldehyde and/or acetals of at least 0.01 wt. % or at least 0.5 wt. %. The amount of ethyl acetate may be considerably higher than acetaldehyde and/or acetal, such as at least 2 wt. % or at least 5 wt. %. In addition, the first reaction mixture in line 108 also comprises hydrogen and other gases that may be used in second reaction zone 103. Thus, in one embodiment, it is not necessary to feed additional hydrogen directly to second reaction zone 103, although in other embodiments fresh hydrogen may be added as necessary.

When separate vessels are used for the first and second reaction zones, such as those shown in FIG. 1A, the first reaction mixture in line 108 may pass through one or more heat exchangers for condensing line 108. Preferably, line 108 is cooled by at least at least 20° C., e.g., at least 50° C. or at least 100° C. In some embodiments, a heat exchanger may transfer heat to another stream in the process through an indirect-contact heat exchanger. Preferred heat exchangers that may be used in embodiments of the present invention include spiral tube heat exchanges, double-pipe heat exchangers, shell and tube heat exchangers, or fluidized-bed heat exchangers. In FIG. 1B, first reaction mixture is passed directly to second reaction zone 103 in a single vessel. As with the embodiment of FIG. 1A, an optional cooling mechanism, not shown, may be provided between the two zones.

Second reaction zone 103 contains a heterogeneous or homogenous catalyst for hydrogenating the one or more impurities, e.g., acetaldehyde, ethyl acetate, and/or acetals, in the first reaction mixture in line 108. The catalyst in the second reaction zone 103 may be the same, similar to the heterogeneous catalyst in the first reaction zone 102. In one embodiment, the second reaction zone 103 reduces the concentration of at least one of the ethyl acetate, acetaldehyde, and/or acetals in the first reaction mixture in line 108 by operating at a lower temperature than the first hydrogenation reaction zone 102 to produce a second reaction mixture 109. Without being bound by theory, the acetaldehyde and ethyl acetate may be reduced by hydrogenation and the acetal reduced by hydrolysis and/or hydrogenation. Although second reaction zone 103 may also hydrogenate acetic acid to form additional ethanol, it has surprisingly and unexpectedly been discovered that concentrations of acetaldehyde and acetals may be preferentially be reduced to a greater extent. Ethyl acetate concentrations may also be reduced in the second reactor. For example, in some embodiments, less than 50% of the acetic acid in first reaction mixture is converted in the second reaction zone, e.g., less than 20% or less than 10%. In some embodiments, substantially none of the acetic acid in the first reaction mixture in line 108 is converted in the second reaction zone 103. By selectively reducing the concentration of at least one of ethyl acetate, acetaldehyde, and/or acetal, the present invention advantageously improves ethanol yield.

The pressure in second reaction zone 103 may be similar to first reaction zone 102, and may range, for example, from 10 kPa to 3000 kPa, e.g., from 50 kPa to 2300 kPa, or from 100 kPa to 1500 kPa. The first reaction mixture optionally is fed to the second reaction zone 103 at a gas hourly space velocity (GHSV) of greater than 500 hr$^{-1}$, e.g., greater than 1000 hr$^{-1}$, greater than 1500 hr$^{-1}$ or greater than 4500 hr$^{-1}$. In terms of ranges, the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1500 hr$^{-1}$ to 8000 hr$^{-1}$. The second reaction zone 103 may comprise a tickle bed reactor, a fixed bed reactor, or any commercial suitable reactor.

As discussed above, the concentration of one or more of the impurities selected from the group consisting of ethyl acetate, acetaldehyde, and/or acetal preferably are less in the second reaction mixture than the in the first reaction mixture. In one embodiment, the total concentration of ethyl acetate, acetaldehyde, and acetal in the second reaction mixture is at least 20% less than the total concentration of ethyl acetate, acetaldehyde, and/or acetal in the first reaction mixture, e.g., at least 25% less, or at least 30% less. In terms of ranges, the total concentration of ethyl acetate, acetaldehyde, and acetal in the second reaction mixture is from 20% to 99% less than the total concentration of ethyl acetate, acetaldehyde, and acetal in the first reaction mixture, and more preferably from 20% to 50%.

In another embodiment, the total concentration of acetaldehyde and acetal, exclusive of the ethyl acetate, is reduced by at least 50% using the secondary reactor, e.g., reduced by at least 70% or at least 90%. In terms of ranges, the total concentration of acetaldehyde and acetal, exclusive of ethyl acetate, in the second reaction mixture is from 50% to 99% less than the total concentration of acetaldehyde and acetal in the first reaction mixture, and more preferably from 70% to 98%.

For ethyl acetate concentration, the second reaction mixture may comprise at least 5% less ethyl acetate than the first reaction mixture, e.g., at least 8% less, or at least 10% less. For acetaldehyde concentration, the second reaction mixture may comprise at least 50% less acetaldehyde than the first reaction mixture, e.g., at least 70% less, or at least 90% less. Similarly, the second reaction mixture may comprise at least 50% less acetal than the first reaction mixture, e.g., at least 70% less, or at least 90% less. Using diethyl acetal as an example, the second reaction mixture may reduce the diethyl acetal concentration by at least 50% compared to the first reaction mixture, e.g., at least 70%, or at least 90%.

An exemplary comparison by hydrogenating acetic acid of the first reaction mixture and second reaction mixture is provided in Table 1. As shown, an advantageous reduction in impurity concentrations may be obtained by using a second reaction zone that operates at reduced temperature. The compositions in Table 1 exclude hydrogen and other gases.

TABLE 1

Reaction Mixtures

| | Conc. (wt. %) | Conc. (wt. %) | Conc. (wt. %) |
|---|---|---|---|
| First Reaction Mixture | | | |
| Ethanol | 5 to 70 | 15 to 70 | 25 to 55 |
| Acetic Acid | 0 to 90 | 0.5 to 70 | 1 to 50 |
| Water | 5 to 40 | 5 to 30 | 10 to 26 |
| Ethyl Acetate | 0 to 30 | 0.1 to 20 | 3 to 10 |
| Acetaldehyde | 0.01 to 10 | 0.1 to 5 | 0.5 to 3 |
| Diethyl acetal | 0.01 to 10 | 0.1 to 5 | 0.5 to 3 |
| Others | 0.1 to 10 | 0.1 to 6 | — |
| Second Reaction Mixture | | | |
| Ethanol | 10 to 80 | 20 to 75 | 30 to 60 |
| Acetic Acid | 0 to 90 | 0.5 to 70 | 1 to 50 |
| Water | 5 to 40 | 5 to 30 | 10 to 26 |
| Ethyl Acetate | 0 to 28 | 0.1 to 19 | 3 to 10 |
| Acetaldehyde | 0.0001 to 1 | 0.001 to 0.5 | 0.005 to 0.05 |
| Diethyl acetal | 0.0001 to 1 | 0.001 to 0.5 | 0.005 to 0.05 |
| Others | 0.1 to 10 | 0.1 to 6 | — |

Table 2 demonstrates the reduction in impurities of ethyl acetate, acetaldehyde, and/or diethyl acetate of the reaction mixture that exits the second reactor. In one embodiment, the total impurity concentration of acetaldehyde and acetal concentration in the second reaction mixture in line 109 is less than 1 wt. %, e.g., less than 0.5 wt. % or less than 0.05 wt. %. In some embodiments, there may be a very low amount of acetaldehyde and acetal, in the second reaction mixture in line 109, e.g., less than 100 wppm or less than 50 wppm, and more preferably the second reaction mixture is substantially free of at least one of acetaldehyde and/or acetal.

Each reaction zone may include a variety of configurations using a fixed bed reactor or a fluidized bed reactor. The first and second reaction zones may have the same type of reactor configuration or may use different reactor configurations. Preferably, each reaction zone is operated in the vapor phase, although the second reaction zone may be operated in the liquid phase. In many embodiments, an "adiabatic" reactor can be used for either or both reaction zones; that is, there is little or no need for internal plumbing through the reaction zone to add or remove heat. In other embodiments, a radial flow reactor or reactors may be employed in each reaction zone, or a series of reactors may be employed in each reaction zone with or without heat exchange, quenching, or introduction of additional feed material. Alternatively, a shell and tube reactor provided with a heat transfer medium may be used. The reaction zones may be housed in a single vessel or each reaction zone may be housed in a series of vessels with heat exchangers therebetween.

In preferred embodiments, a catalyst is employed in a fixed bed reactor, e.g., in the shape of a pipe or tube, where the reactants, typically in vapor form, are passed over or through the catalyst. Other reactors, such as fluid or ebullient bed reactors, can be employed. In some instances, a hydrogenation catalyst may be used in conjunction with an inert material to regulate the pressure drop of the reactant stream through the catalyst bed and the contact time of the reactant compounds with the catalyst particles.

Contact or residence time in each reaction zone can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

Hydrogenation of Acetic Acid in First Reaction Zone

The step of hydrogenating acetic acid in the first reaction zone may use any suitable hydrogenation process for producing ethanol. The materials, catalysts, reaction conditions, and separation processes that may be used in the hydrogenation of acetic acid are described further below. In some embodiments, the catalysts described for the first reaction zone may also be used in the second reaction zone.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the first reaction zone may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the first reaction zone of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

In the first reaction zone, the hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

Catalysts similar to those described for the first reaction zone may also be used in the second reaction zone. In another embodiment, however, the second reaction zone may employ a different catalyst from the first reaction zone.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, or $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid in the first reaction zone may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol in the first reaction zone is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

Ethanol Recovery

Returning to FIGS. 1A and 1B, the second reaction mixture in line 109 may be condensed and fed to a separator 110, which, in turn, provides a vapor stream 111 and a liquid stream 112. In some embodiments, separator 110 may comprise a flasher or a knockout pot. The separator 110 may operate at a temperature of from 20° C. to 250° C., e.g., from 30° C. to 225° C. or from 60° C. to 200° C. The pressure of separator 110 may be from 50 kPa to 2000 kPa, e.g., from 75 kPa to 1500 kPa or from 100 kPa to 1000 kPa. Optionally, the crude ethanol product in line 109 may pass through one or more membranes to separate hydrogen and/or other non-condensable gases.

The vapor stream 111 exiting separator 110 may comprise hydrogen and hydrocarbons, and may be purged and/or returned to reaction zone 101. When returned to first reaction zone 102, vapor stream 110 is combined with the hydrogen feed 104 and co-fed to vaporizer 106. In some embodiments, the returned vapor stream 111 may be compressed before being combined with hydrogen feed 104 and initially fed to the first reaction zone 102.

Figure 2:
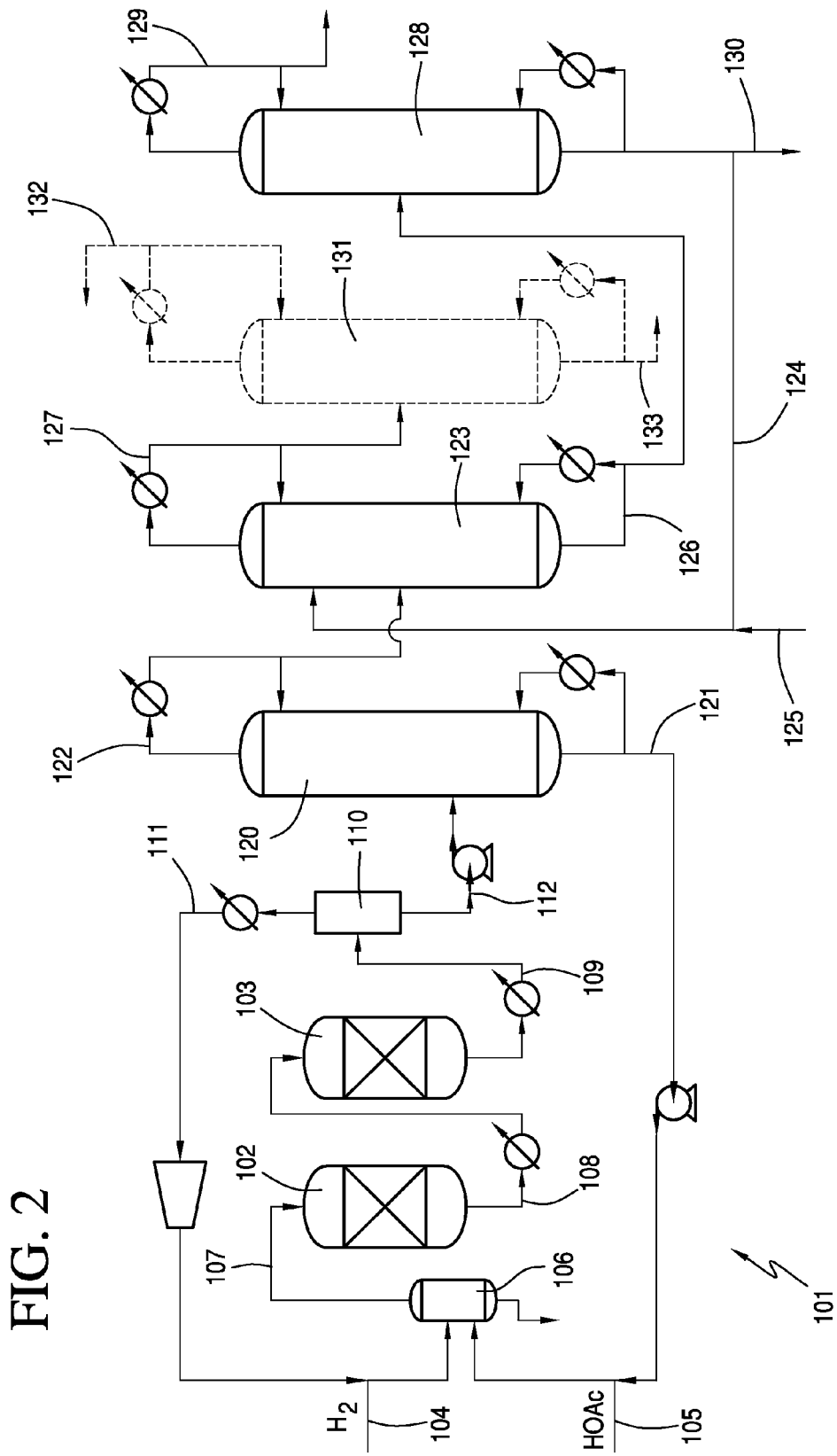
FIG. 2 is a schematic diagram of a hydrogenation process having at least three separation columns in accordance with one embodiment of the present invention.
Figure 3:
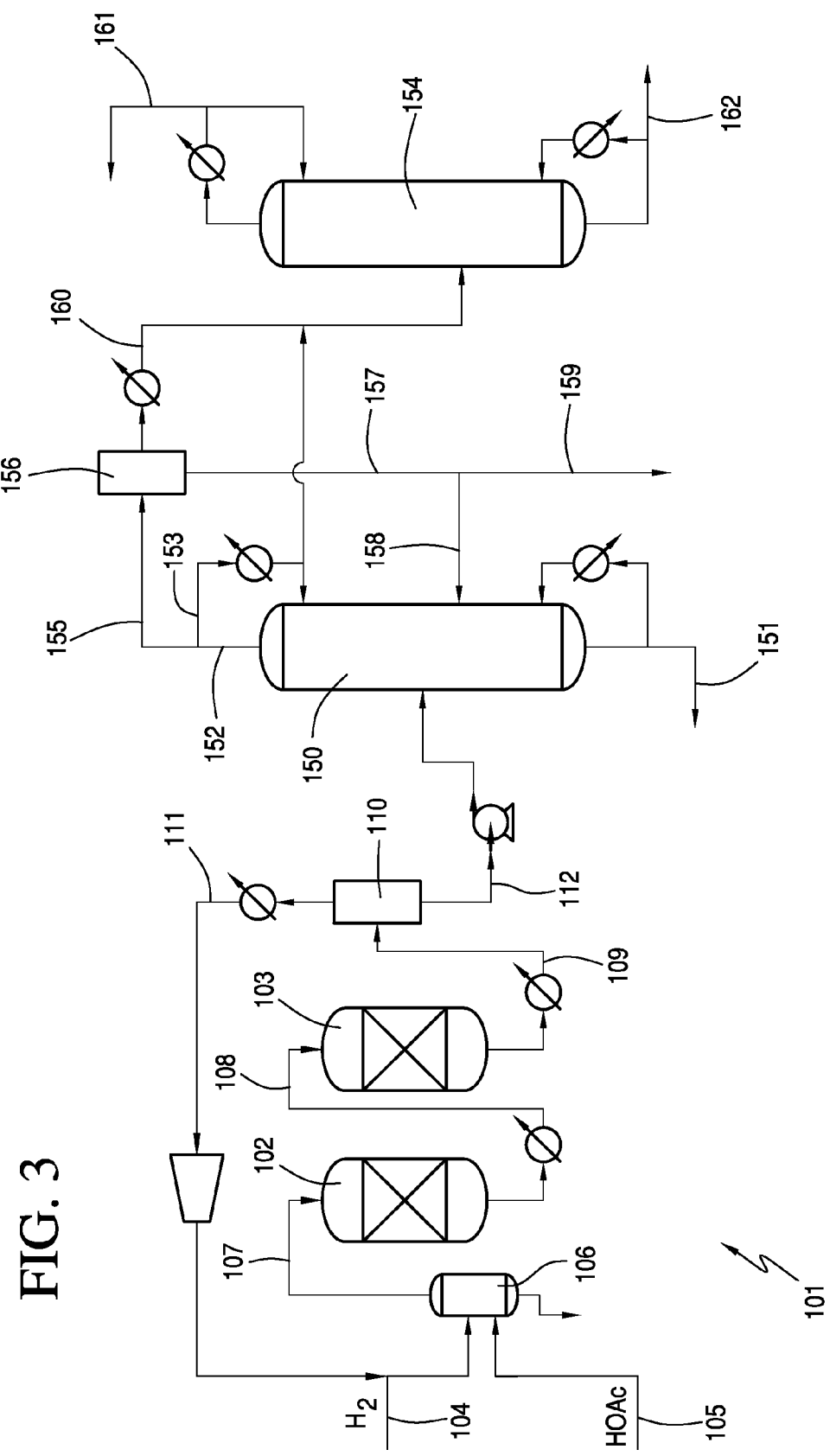
FIG. 3 is a schematic diagram of a hydrogenation process having two separation columns and a water separation unit in accordance with one embodiment of the present invention.
Figure 4:
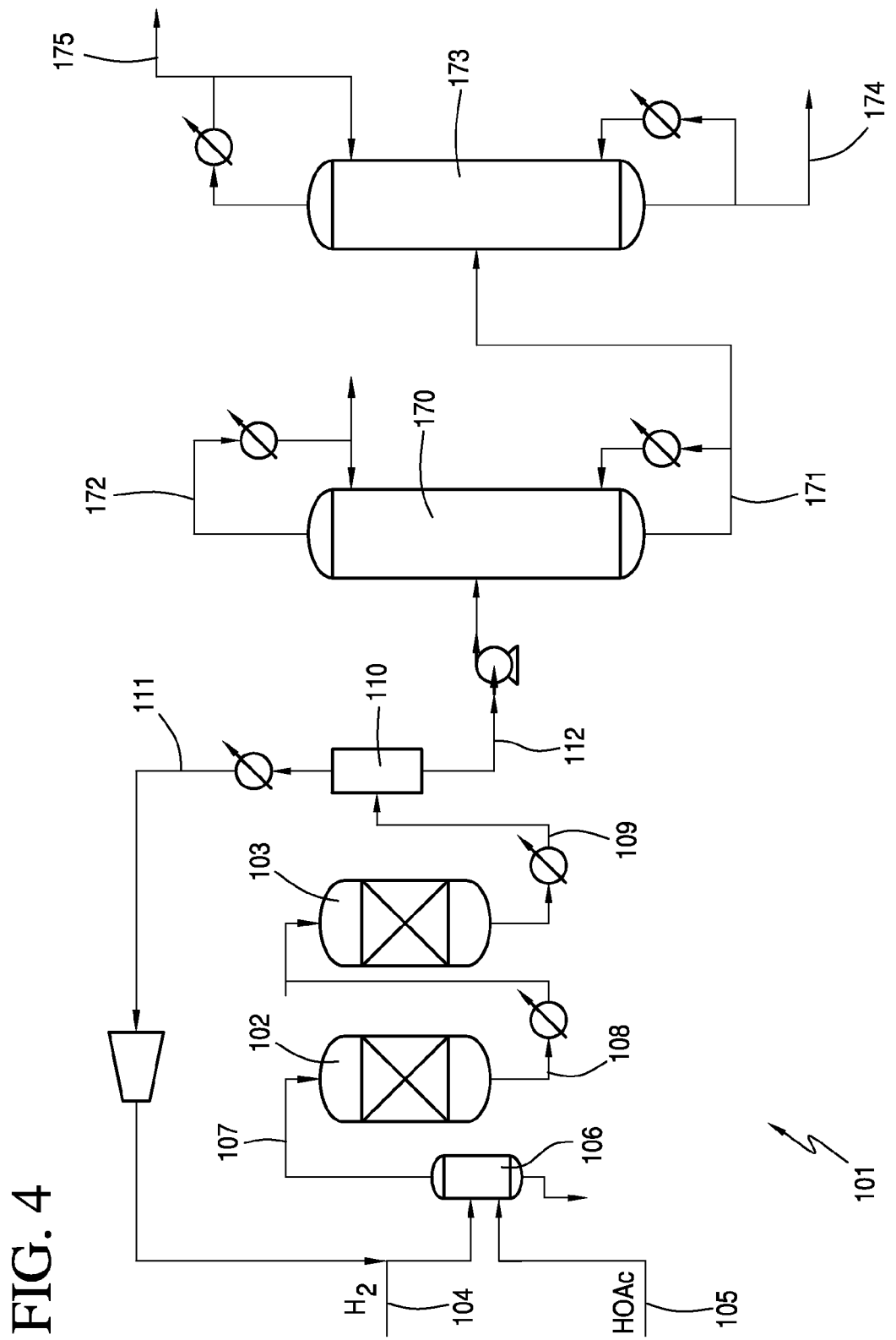
FIG. 4 is a schematic diagram of a hydrogenation process having two separation columns in accordance with one embodiment of the present invention.

In FIGS. 1A and 1B, the liquid stream 112 from separator 110 is withdrawn and further processed to recover ethanol. FIGS. 2, 3, and 4 are exemplary separation schemes suitable for recovering ethanol. Although the exemplary embodiments shown in FIGS. 2, 3, and 4 use separate vessels for the first reaction zone and second reaction zone, in other embodiments, the reaction zones for FIGS. 2, 3, and 4, may be in the same vessel as shown in FIG. 1B. Other separation systems may be used with embodiments of the present invention.

In FIG. 2, liquid stream 112 is pumped to the side of first column 120, also referred to as an "acid separation column." In one embodiment, the contents of liquid stream 112 are substantially similar to the second reaction mixture obtained from the second reaction zone, except that the composition has been depleted of hydrogen, carbon dioxide, methane and/or ethane, which are removed by separator 110. Liquid stream 112 would have low concentrations of impurities, e.g., acetaldehyde and acetals. Liquid stream 112 may also be referred to as a crude ethanol product. Exemplary components of liquid stream 112 are provided in Table 2. It should be understood that liquid stream 112 may contain other components, not listed in Table 2.

TABLE 2

| COLUMN FEED COMPOSITION (Liquid Stream 112) | | | |
|---|---|---|---|
| | Conc. (wt. %) | Conc. (wt. %) | Conc. (wt. %) |
| Ethanol | 10 to 80 | 20 to 75 | 30 to 60 |
| Acetic Acid | 0 to 90 | 0.5 to 70 | 1 to 50 |
| Water | 5 to 40 | 5 to 30 | 10 to 26 |
| Ethyl Acetate | 0 to 28 | 0.1 to 19 | 3 to 10 |
| Acetaldehyde | <1 | 0.001 to 0.5 | 0.005 to 0.05 |
| Acetals | <1 | 0.001 to 0.5 | 0.005 to 0.05 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, second reaction mixture in line 109 or liquid stream 112 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

In the embodiment shown in FIG. 2, line 112 is introduced in the lower part of first column 120, e.g., lower half or lower third. In first column 120, unreacted acetic acid, a portion of the water, and other heavy components, if present, are removed from the composition in line 121 and are withdrawn, preferably continuously, as residue. Some or all of the residue may be returned and/or recycled back to reaction zone 101 via line 121. Recycling the acetic acid in line 121 to the vaporizer 106 may reduce the amount of heavies that need to be purged from vaporizer 106. Reducing the amount of heavies to be purged may improve efficiencies of the process while reducing byproducts.

First column 120 also forms an overhead distillate, which is withdrawn in line 122, and which may be condensed and refluxed, for example, at a ratio of from 10:1 to 1:10, e.g., from 3:1 to 1:3 or from 1:2 to 2:1.

When column 120 is operated under standard atmospheric pressure, the temperature of the residue exiting in line 121 preferably is from 95° C. to 120° C., e.g., from 110° C. to 117° C. or from 111° C. to 115° C. The temperature of the distillate exiting in line 122 preferably is from 70° C. to 110° C., e.g., from 75° C. to 95° C. or from 80° C. to 90° C. Column 120 preferably operates at ambient pressure. In other embodiments, the pressure of first column 120 may range from 0.1 KPa to 510 KPa, e.g., from 1 KPa to 475 KPa or from 1 KPa to 375 KPa. Exemplary components of the distillate and residue compositions for first column 120 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

ACID COLUMN 120 (FIG. 2)

| | Conc. (wt. %) | Conc. (wt. %) | Conc. (wt. %) |
|---|---|---|---|
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <1 | 0.001 to 0.5 | 0.005 to 0.05 |
| Acetal | <1 | 0.001 to 0.5 | 0.01 to 0.5 |
| Acetone | <1 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column 120, the acetal appears to decompose in the column such that less or even no detectable amounts are present in the distillate and/or residue.

The distillate in line 122 preferably comprises ethanol, ethyl acetate, and water, along with other impurities, which may be difficult to separate due to the formation of binary and tertiary azeotropes. To further separate distillate, line 122 is introduced to the second column 123, also referred to as the "light ends column," preferably in the middle part of column 123, e.g., middle half or middle third. Preferably the second column 123 is an extractive distillation column, and an extraction agent is added thereto via lines 124 and/or 125. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 122 that is fed to the second column 123 comprises ethyl acetate, ethanol, and water. These compounds tend to form binary and ternary azeotropes, which decrease separation efficiency. As shown, in one embodiment the extraction agent comprises the third residue in line 124. Preferably, the recycled third residue in line 124 is fed to second column 123 at a point higher than the first distillate in line 122. In one embodiment, the recycled third residue in line 124 is fed near the top of second column 123 or fed, for example, above the feed in line 122 and below the reflux line from the condensed overheads. In a tray column, the third residue in line 124 is continuously added near the top of the second column 123 so that an appreciable amount of the third residue is present in the liquid phase on all of the trays below. In another embodiment, the extraction agent is fed from a source outside of the process 100 via line 125 to second column 123. Preferably this extraction agent comprises water.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 123. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 124 and co-fed to the second column 123. The additional extraction agent may also be added separately to the second column 123. In one aspect, the extraction agent comprises an extraction agent, e.g., water, derived from an external source via line 125 and none of the extraction agent is derived from the third residue.

Second column 123 may be a tray or packed column. In one embodiment, second column 123 is a tray column having from 5 to 70 trays, e.g., from 15 to 50 trays or from 20 to 45 trays. Although the temperature and pressure of second column 123 may vary, when at atmospheric pressure the temperature of the second residue exiting in line 126 preferably is from 60° C. to 90° C., e.g., from 70° C. to 90° C. or from 80° C. to 90° C. The temperature of the second distillate exiting in line 127 from second column 123 preferably is from 50° C. to 90° C., e.g., from 60° C. to 80° C. or from 60° C. to 70° C. Column 123 may operate at atmospheric pressure. In other embodiments, the pressure of second column 123 may range from 0.1 kPa to 510 kPa, e.g., from 1 kPa to 475 kPa or from 1 kPa to 375 kPa. Exemplary components for the distillate and residue compositions for second column 123 are provided in Table 4 below. Any remaining impurities from the second reaction mixture are generally concentrated in the second distillate in FIG. 2. It should be understood that the distillate and residue may also contain other components, not listed, such as components in the feed.

TABLE 4

SECOND COLUMN 123 (FIG. 2)

|  | Conc. (wt. %) | Conc. (wt. %) | Conc. (wt. %) |
|---|---|---|---|
| Distillate |  |  |  |
| Ethyl Acetate | 10 to 99 | 25 to 95 | 50 to 93 |
| Acetaldehyde | <5 | 0.005 to 2 | 0.01 to 1 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

In preferred embodiments, the recycling of the third residue promotes the separation of ethyl acetate from the residue of the second column 123. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 123, the weight ratio of ethyl acetate in the second residue to ethyl acetate in the second distillate approaches zero.

The weight ratio of ethanol in the second residue to second distillate preferably is at least 3:1, e.g., at least 6:1, at least 8:1, at least 10:1 or at least 15:1. All or a portion of the third residue is recycled to the second column. In one embodiment, all of the third residue may be recycled until process reaches a steady state and then a portion of the third residue is recycled with the remaining portion being purged from the system. The composition of the second residue will tend to have lower amounts of ethanol than when the third residue is not recycled. As the third residue is recycled, the composition of the second residue, as provided in Table 4, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 123, which comprises ethanol and water, is fed via line 126 to third column 128, also referred to as the "product column." More preferably, the second residue in line 126 is introduced in the lower part of third column 128, e.g., lower half or lower third. Third column 128 recovers ethanol, which preferably is substantially pure with respect to organic impurities and other than the azeotropic water content, as the distillate in line 129. The distillate of third column 128 preferably is refluxed as shown in FIG. 2, for example, at a reflux ratio of from 1:10 to 10:1, e.g., from 1:3 to 3:1 or from 1:2 to 2:1. The third residue in line 124, which comprises primarily water, preferably is returned to the second column 123 as an extraction agent as described above. In one embodiment, a first portion of the third residue in line 124 is recycled to the second column and a second portion is purged and removed from the system via line 130. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Although FIG. 2 shows third residue being directly recycled to second column 123, third residue may also be returned indirectly, for example, by storing a portion or all of the third residue in a tank (not shown) or treating the third residue to further separate any minor components such as aldehydes, higher molecular weight alcohols, or esters in one or more additional columns (not shown).

Third column 128 is preferably a tray column as described above and operates at atmospheric pressure or optionally at pressures above or below atmospheric pressure. The temperature of the third distillate exiting in line 129 preferably is from 60° C. to 110° C., e.g., from 70° C. to 100° C. or from 75° C. to 95° C. The temperature of the third residue in line 124 preferably is from 70° C. to 115° C., e.g., from 80° C. to 110° C. or from 85° C. to 105° C. Exemplary components of the distillate and residue compositions for third column 128 are provided in Table 5 below. It should be understood that the distillate and residue may also contain other components, not listed, such as components in the feed.

TABLE 5

THIRD COLUMN 128 (FIG. 2)

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |
| Ethyl Acetate | <12 | 0.0001 to 0.05 | 0.005 to 0.025 |
| Acetaldehyde | <0.1 | 0.0001 to 0.05 | 0.005 to 0.025 |
| Diethyl Acetal | <0.1 | 0.0001 to 0.05 | 0.005 to 0.025 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

In one embodiment, the third residue in line 124 is withdrawn from third column 128 at a temperature higher than the operating temperature of the second column 123. Preferably, the third residue in line 124 is integrated to heat one or more other streams or is reboiled prior to be returned to the second column 123.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns in the system 100. Preferably at least one side stream is used to remove impurities from the third column 128. The impurities may be purged and/or retained within the system 100.

The third distillate in line 129 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 123, the second distillate preferably is refluxed as shown in FIG. 2, optionally at a reflux ratio of 1:10 to 10:1, e.g., from 1:5 to 5:1 or from 1:3 to 3:1. The second distillate in line 127 may be purged or recycled to the reaction zone. In an optional embodiment, the second distillate in line 127 may be further processed in an optional fourth column 131, also referred to as the "acetaldehyde removal column." Whether optional fourth column 131 is required depends primarily on the acetaldehyde concentration in line 127. In fourth column 131 the second distillate is separated into a fourth distillate, which comprises acetaldehyde, in line 132 and a fourth residue, which comprises ethyl acetate, in line 133. The fourth distillate preferably is refluxed at a reflux ratio of from 1:20 to 20:1, e.g., from 1:15 to 15:1 or from 1:10 to 10:1, and a portion of the fourth distillate is returned to the reaction zone 101. For example, the fourth distillate may be combined with the acetic acid feed, added to the vaporizer 106, or added directly to the reactor 103. The fourth distillate preferably is co-fed with the acetic acid in feed line 105 to vaporizer 106. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of fourth column 131 may be purged via line 133. The fourth residue primarily comprises ethyl acetate and ethanol, which may be suitable for use as a solvent mixture or in the production of esters. In one preferred embodiment, the acetaldehyde is removed from the second distillate in fourth column 131 such that no detectable amount of acetaldehyde is present in the residue of column 131.

Fourth column 131 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 131 may operate at a pressure that is higher than the pressure of the other columns.

The temperature of the fourth distillate exiting in line 132 preferably is from 60° C. to 110° C., e.g., from 70° C. to 100° C. or from 75° C. to 95° C. The temperature of the residue in line 133 preferably is from 70° C. to 115° C., e.g., from 80° C. to 110° C. or from 85° C. to 110° C. Exemplary components of the distillate and residue compositions for fourth column 131 are provided in Table 6 below. It should be understood that the distillate and residue may also contain other components, not listed, such as components in the feed.

TABLE 6

OPTIONAL FOURTH COLUMN 131 (FIG. 2)

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

In one embodiment, a portion of the third residue in line 124 is recycled to second column 123. In one embodiment, recycling the third residue further reduces the aldehyde components in the second residue and concentrates these aldehyde components in second distillate in line 127 and thereby sent to the fourth column 131, wherein the aldehydes may be more easily separated. The third distillate, e.g. intermediate stream, in line 129 may have lower concentrations of aldehydes and esters due to the recycling of third residue in line 124.

FIG. 3 illustrates another exemplary separation system to recover ethanol from the second reaction mixture. Liquid stream 112 is introduced in the middle or lower portion of a first column 150, also referred to as acid-water column. For purposes of convenience, the columns in each exemplary separation process, may be referred as the first, second, third, etc., columns, but it is understood that first column 150 in FIG. 3 operates differently than the first column 120 of FIG. 2. In one embodiment, no entrainers are added to first column 150. In FIG. 3, first column 150, water and unreacted acetic acid, along with any other heavy components, if present, are removed from liquid stream 112 and are withdrawn, preferably continuously, as a first residue in line 151. Preferably, a substantial portion of the water in the crude ethanol product that is fed to first column 150 may be removed in the first residue, for example, up to about 90% of the water from the crude ethanol product, and more preferably up to about 75%. First column 150 also forms a first distillate, which is withdrawn in line 152.

When column 150 is operated under about 170 kPa, the temperature of the residue exiting in line 151 preferably is from 90° C. to 130° C., e.g., from 95° C. to 120° C. or from 100° C. to 115° C. The temperature of the distillate exiting in line 152 preferably is from 60° C. to 90° C., e.g., from 65° C. to 85° C. or from 70° C. to 80° C. In some embodiments, the pressure of first column 150 may range from 0.1 kPa to 510 kPa, e.g., from 1 kPa to 475 kPa or from 1 kPa to 375 kPa.

The first distillate in line 152 comprises water, in addition to ethanol and other organics. In terms of ranges, the concentration of water in the first distillate in line 152 preferably is from 4 wt. % to 38 wt. %, e.g., from 7 wt. % to 32 wt. %, or from 7 to 25 wt. %. A portion of first distillate in line 153 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 150. The condensed portion of the first distillate may also be fed to a second column 154.

The remaining portion of the first distillate in 155 is fed to a water separation unit 156. Water separation unit 156 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separation unit 156 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. Water separation unit 156 may remove at least 95% of the water from the portion of first distillate in line 155, and more preferably from 99% to 99.99% of the water from the first distillate, in a water stream 157. All or a portion of water stream 157 may be returned to column 150 in line 158, where the water preferably is ultimately recovered from column 150 in the first residue in line 151. Additionally or alternatively, all or a portion of water stream 157 may be purged via line 159. The remaining portion of first distillate exits the water separation unit 156 as ethanol mixture stream 160. Ethanol mixture stream 160 may have a low concentration of water of less than 10 wt. %, e.g., less than 6 wt. % or less than 2 wt. %. Exemplary components of ethanol mixture stream 160 and first residue in line 151 are provided in Table 7 below. It should also be understood that these streams may also contain other components, not listed, such as components derived from the feed.

TABLE 7

FIRST COLUMN 150 WITH PSA (FIG. 3)

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <1 | 0.001 to 0.5 | 0.005 to 0.05 |
| Acetal | <0.1 | <0.05 | <0.01 |
| Acetone | <0.05 | 0.001 to 0.03 | 0.01 to 0.025 |
| Residue |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 160 is not returned or refluxed to first column 150. The condensed portion of the first distillate in line 153 may be combined with ethanol mixture stream 160 to control the water concentration fed to the second column 154. For example, in some embodiments the first distillate may be split into equal portions, while in other embodiments, all of the first distillate may be condensed or all of the first distillate may be processed in the water separation unit. In FIG. 3, the condensed portion in line 153 and ethanol mixture stream 160 are co-fed to second column 154. In other embodiments, the condensed portion in line 153 and ethanol mixture stream 160 may be separately fed to second column 154. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 154 in FIG. 3, also referred to as the "light ends column," removes ethyl acetate and acetaldehyde from the first distillate in line 153 and/or ethanol mixture stream 160. Ethyl acetate and acetaldehyde are removed as a second distillate in line 161 and ethanol is removed as the second residue in line 162. Second column 154 may be a tray column or packed column. In one embodiment, second column 154 is a tray column having from 5 to 70 trays, e.g., from 15 to 50 trays or from 20 to 45 trays.

Second column 154 operates at a pressure ranging from 0.1 kPa to 510 kPa, e.g., from 10 kPa to 450 kPa or from 50 kPa to 350 kPa. Although the temperature of second column 154 may vary, when at about 20 kPa to 70 kPa, the temperature of the second residue exiting in line 162 preferably is from 30° C. to 75° C., e.g., from 35° C. to 70° C. or from 40° C. to 65° C. The temperature of the second distillate exiting in line 161 preferably is from 20° C. to 55° C., e.g., from 25° C. to 50° C. or from 30° C. to 45° C.

The total concentration of water fed to second column 154 preferably is less than 10 wt. %, as discussed above. When first distillate in line 153 and/or ethanol mixture stream 160 comprises minor amounts of water, e.g., less than 1 wt. % or less than 0.5 wt. %, additional water may be fed to the second column 154 as an extractive agent in the upper portion of the column. A sufficient amount of water is preferably added via the extractive agent such that the total concentration of water fed to second column 154 is from 1 to 10 wt. % water, e.g., from 2 to 6 wt. %, based on the total weight of all components fed to second column 154. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 154 are provided in Table 8, below. It should be understood that the distillate and residue may also contain other components, not listed in Table 8.

TABLE 8

SECOND COLUMN 154 (FIG. 3)

|  | Conc. (wt. %) | Conc. (wt. %) | Conc. (wt. %) |
|---|---|---|---|
| Second Distillate |  |  |  |
| Ethyl Acetate | 5 to 90 | 10 to 80 | 15 to 75 |
| Acetaldehyde | <5 | 0.005 to 2 | 0.01 to 1 |
| Ethanol | <45 | 0.001 to 40 | 0.01 to 35 |
| Water | <20 | 0.01 to 10 | 0.1 to 5 |
| Second Residue |  |  |  |
| Ethanol | 80 to 99.5 | 85 to 99.5 | 90 to 99.5 |
| Water | <20 | 0.001 to 15 | 0.01 to 10 |

TABLE 8-continued

SECOND COLUMN 154 (FIG. 3)

|  | Conc. (wt. %) | Conc. (wt. %) | Conc. (wt. %) |
|---|---|---|---|
| Ethyl Acetate | <1 | 0.001 to 2 | 0.001 to 0.5 |
| Acetic Acid | <0.5 | <0.01 | 0.001 to 0.01 |

The second distillate in line 161, which comprises ethyl acetate and/or acetaldehyde, preferably is refluxed as shown in FIG. 3, for example, at a reflux ratio of from 1:30 to 30:1, e.g., from 1:10 to 10:1 or from 1:3 to 3:1. In one aspect, not shown, the second distillate 161 or a portion thereof may be returned to first reaction zone 102. The ethyl acetate and/or acetaldehyde in the second distillate may be further reacted in first reaction zone 102.

In optional embodiment, the second distillate in line 161 and/or a refined second distillate, or a portion of either or both streams, may be further separated to produce an acetaldehyde-containing stream and an ethyl acetate-containing stream similar to optional fourth column in FIG. 2. This may allow a portion of either the resulting acetaldehyde-containing stream or ethyl acetate-containing stream to be recycled to reactor 108 while purging the other stream. The purge stream may be valuable as a source of either ethyl acetate and/or acetaldehyde.

FIG. 4 is another exemplary separation system to recover ethanol from the second reaction mixture. Liquid stream 112 is introduced in the upper part of first column 170, e.g., upper half or upper third. In one embodiment, no entrainers are added to first column 170. In first column 170, a weight majority of the ethanol, water, acetic acid, and other heavy components, if present, are removed from liquid stream 112 and are withdrawn, preferably continuously, as residue in line 171. First column 170 also forms an overhead distillate, which is withdrawn in line 172, and which may be condensed and refluxed, for example, at a ratio of from 30:1 to 1:30, e.g., from 10:1 to 1:10 or from 1:5 to 5:1. The overhead distillate in stream 172 preferably comprises a weight majority of the ethyl acetate from liquid stream 112.

When column 170 is operated under about 170 kPa, the temperature of the residue exiting in line 171 preferably is from 70° C. to 155° C., e.g., from 90° C. to 130° C. or from 100° C. to 110° C. The base of column 170 may be maintained at a relatively low temperature by withdrawing a residue stream comprising ethanol, water, and acetic acid, thereby providing an energy efficiency advantage. The temperature of the distillate exiting in line 172 preferably at 170 kPa is from 75° C. to 100° C., e.g., from 75° C. to 83° C. or from 81° C. to 84° C. In some embodiments, the pressure of first column 170 may range from 0.1 kPa to 510 kPa, e.g., from 1 kPa to 475 kPa or from 1 kPa to 375 kPa. Exemplary components of the distillate and residue compositions for first column 170 are provided in Table 9 below. It should also be understood that the distillate and residue may also contain other components, not listed in Table 9.

TABLE 9

FIRST COLUMN 170 (FIG. 4)

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | <0.1 | 0.0001 to 0.05 | 0.005 to 0.025 |

TABLE 9-continued

FIRST COLUMN 170 (FIG. 4)

|  | Conc. (wt. %) | Conc. (wt. %) | Conc. (wt. %) |
|---|---|---|---|
| Acetal | <0.1 | 0.0001 to 0.05 | 0.005 to 0.025 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue |  |  |  |
| Acetic Acid | 0.01 to 35 | 0.1 to 30 | 0.2 to 25 |
| Water | 25 to 70 | 30 to 65 | 35 to 60 |
| Ethanol | 10 to 75 | 15 to 70 | 20 to 65 |

In an embodiment of the present invention, column 170 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 171 to water in the distillate in line 172 may be greater than 1:1, e.g., greater than 2:1. The weight ratio of ethanol in the residue to ethanol in the distillate may be greater than 1:1, e.g., greater than 2:1

The amount of acetic acid in the first residue may vary depending primarily on the conversion in first reaction zone 102 and/or second reaction zone 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 ppm, less than 500 ppm or less than 100 ppm acetic acid. The distillate may be purged from the system or recycled in whole or part to first reaction zone 102. In some embodiments, the distillate may be further separated, e.g., in a distillation column (not shown), into an acetaldehyde stream and an ethyl acetate stream. Either of these streams may be returned to the first reaction zone 102 or separated from system as a separate product.

Some species, such as acetals, may decompose in first column 170 such that very low amounts, or even no detectable amounts, of acetals remain in the distillate or residue.

To recover ethanol, the residue in line 171 may be further separated in a second column 173, also referred to as an "acid separation column." An acid separation column may be used when the acetic acid concentration in the first residue is greater than 1 wt. %, e.g., greater than 5 wt. %. The first residue in line 171 is introduced to second column 173 preferably in the top part of column 173, e.g., top half or top third. Second column 173 yields a second residue in line 174 comprising acetic acid and water, and a second distillate in line 175 comprising ethanol. Second column 173 may be a tray column or packed column. In one embodiment, second column 173 is a tray column having from 5 to 150 trays, e.g., from 15 to 50 trays or from 20 to 45 trays. Although the temperature and pressure of second column 173 may vary, when at atmospheric pressure the temperature of the second residue exiting in line 174 preferably is from 95° C. to 130° C., e.g., from 100° C. to 125° C. or from 110° C. to 120° C. The temperature of the second distillate exiting in line 175 preferably is from 60° C. to 105° C., e.g., from 75° C. to 100° C. or from 80° C. to 100° C. The pressure of second column 173 may range from 0.1 kPa to 510 kPa, e.g., from 1 kPa to 475 kPa or from 1 kPa to 375 kPa. Exemplary components for the distillate and residue compositions for second column 173 are provided in Table 10 below. It should be understood that the distillate and residue may also contain other components, not listed in Table 10.

TABLE 10

SECOND COLUMN 173 (FIG. 4)

|  | Conc. (wt. %) | Conc. (wt. %) | Conc. (wt. %) |
|---|---|---|---|
| Second Distillate |  |  |  |
| Ethanol | 70 to 99.9 | 75 to 99.5 | 80 to 99.5 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 0.5 to 25 | 0.5 to 20 |
| Second Residue |  |  |  |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 175 to ethanol in the second residue in line 174 preferably is at least 35:1. In one embodiment, the weight ratio of water in the second residue 174 to water in the second distillate 175 is greater than 2:1, e.g., greater than 4:1 or greater than 6:1. In addition, the weight ratio of acetic acid in the second residue 174 to acetic acid in the second distillate 175 preferably is greater than 10:1, e.g., greater than 15:1 or greater than 20:1. Preferably, the second distillate in line 175 is substantially free of acetic acid and may only contain, if any, trace amounts of acetic acid. Preferably, the second distillate in line 175 contains substantially no ethyl acetate.

The remaining water from the second distillate in line 175 may be removed in further embodiments of the present invention. Depending on the water concentration, the ethanol product may be derived from the second distillate in line 175. Some applications, such as industrial ethanol applications, may tolerate water in the ethanol product, while other applications, such as fuel applications, may require an anhydrous ethanol. The amount of water in the distillate of line 175 may be closer to the azeotropic amount of water, e.g., at least 4 wt. %, preferably less than 20 wt. %, e.g., less than 12 wt. % or less than 7.5 wt. %. Water may be removed from the second distillate in line 175 using several different separation techniques as described herein. Particularly preferred techniques include the use of distillation column, membranes, adsorption units, and combinations thereof.

Some of the residues withdrawn from the separation systems shown in FIGS. 2, 3, and 4, may comprise acetic acid and water. Depending on the amount of water and acetic acid contained in the residue of first column, e.g., 120 in FIG. 2, 150 in FIG. 3, or residue of second column 173 in FIG. 4, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the first reaction zone 102. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The columns shown in figures may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The final ethanol product produced by the processes of the present invention may be taken from a stream that primarily comprises ethanol from FIGS. 2, 3, and 4. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 11.

TABLE 11

FINISHED ETHANOL COMPOSITIONS

| Component | Conc. (wt. %) | Conc. (wt. %) | Conc. (wt. %) |
|---|---|---|---|
| Ethanol | 75 to 99.9 | 80 to 99.5 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 11, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, an example is provided below. It should be understood that these examples are for illustrative purposes only and is not to be construed as limiting the invention in any manner.

EXAMPLES

A first reaction mixture was produced by reacting acetic acid and hydrogen over $SiO_2$—$CaSiO_3$(6%)-Pt(1%)-Sn (1.2%) in three separate runs. The catalyst was carried out at 300° C. and at a pressure of about 2164 kPa. The conversion of acetic acid was approximately 95%. Each of the first reaction mixture was then cooled and fed to a second reaction zone operated at a temperature of 150° C. The pressure of the second reaction zone was the same. Table 12 summarizes the results of the three separate runs. Each run was fed to the second reaction zone at a different space velocity. Run A was fed at 1700 hr$^{-1}$. Run B was fed at 6100 hr$^{-1}$. Run C was fed at 3200 hr$^{-1}$.

TABLE 12

| | Run A | Run B | Run C |
|---|---|---|---|
| First reaction mixture | | | |
| Ethanol | 52.75 | 52.52 | 52.03 |
| Water | 26.91 | 26.94 | 27.62 |
| Ethyl Acetate | 14.30 | 14.24 | 14.10 |
| Acetic Acid | 3.95 | 3.93 | 3.88 |
| Diethyl Acetal | 2.33 | 2.33 | 2.36 |
| Acetaldehyde | 1.01 | 1.01 | 0.98 |
| Second reaction mixture | | | |
| Ethanol | 56.91 | 56.03 | 56.65 |
| Water | 26.47 | 27.89 | 26.59 |
| Ethyl Acetate | 13.11 | 12.96 | 13.33 |

TABLE 12-continued

|  | Run A | Run B | Run C |
|---|---|---|---|
| Acetic Acid | 3.94 | 4.06 | 2.97 |
| Diethyl Acetal | <0.01 | 0.06 | 0.08 |
| Acetaldehyde | 0.05 | 0.06 | 0.03 |

Run A lowered the impurity concentration of acetaldehyde and diethyl acetal, by 95.1% and 99.9%. The ethanol increase of Run A was about 7.3%. Run B lowered the impurity concentration of acetaldehyde and diethyl acetal, by 94.1% and 97.4%. The ethanol increase of Run B was about 6.3%. Run C lowered the impurity concentration of acetaldehyde and diethyl acetal, by 96.9% and 96.6%. The ethanol increase of Run C was about 8.2%.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol comprising:
feeding acetic acid to a reactor vessel comprising the first reaction zone and second reaction zone;
hydrogenating the acetic acid in the first reaction zone operated at a first temperature to form a first reaction mixture comprising ethanol and one or more impurities selected from the group consisting of ethyl acetate, acetaldehyde, acetals, and mixtures thereof;
feeding the first reaction mixture directly to the second reaction zone, without separation;
hydrogenating at least a portion of the one or more impurities in the second reaction zone operated at a second temperature from 50° C. to 225° C., wherein the second temperature is less than the first temperature, to form a second reaction mixture; and
recovering ethanol from the second reaction mixture, wherein the second reaction mixture comprises at least 50% less acetals than the first reaction mixture, at least 50% less acetaldehyde than the first reaction mixture, or at least 5% less ethyl acetate than the first reaction mixture.

2. The process of claim 1, wherein the first temperature is from 125° C. to 350° C.

3. The process of claim 1, wherein the second temperature is at least 20° C. less than the first temperature.

4. The process of claim 1, wherein the acetals are selected from the group consisting of ethyl propyl acetal, ethyl butyl acetal, diethyl acetal, dimethyl acetal, methyl ethyl acetal, and hemiacetals and mixtures thereof.

5. The process of claim 1, wherein the second reaction mixture comprises more ethanol than the first reaction mixture.

6. The process of claim 1, wherein the first reaction zone and the second reaction zone comprise a catalyst comprising a combination of metals selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron.

7. The process of claim 1, wherein the first reaction zone and the second reaction zone comprise a catalyst on a support comprising 0.2 to 3.0 wt. % platinum, 0.2 to 5.0 wt %. tin, wherein the support is selected from the group consisting of silica, silica/alumina, calcium metasilicate, iron oxide, alumina, titania, zirconia, magnesium oxide, carbon, graphite, high surface area graphitized carbon, activated carbons, and mixtures thereof, and optionally the catalyst comprises 0.1 to 20 wt. % of a support modifier selected from the group consisting of $CaSiO_3$, $MgSiO_3$, $TiO_2$, $ZrO_2$, $WO_3$, and $MoO_3$.

8. The process of claim 1, wherein the first reaction zone and the second reaction zone comprise a catalyst on a support comprising 0.2 to 3.0 wt. % palladium and 0.2 to 5.0 wt %. rhenium, wherein the support is selected from the group consisting of silica, silica/alumina, calcium metasilicate, iron oxide, alumina, titania, zirconia, magnesium oxide, carbon, graphite, high surface area graphitized carbon, activated carbons, and mixtures thereof, and optionally the catalyst comprises 0.1 to 20 wt. % of a support modifier selected from the group consisting of $CaSiO_3$, $MgSiO_3$, $TiO_2$, $ZrO_2$, $WO_3$, and $MoO_3$.

9. The process of claim 1, wherein the second reaction mixture comprises ethanol, water, ethyl acetate, acetic acid, and less than 1 wt. % acetal.

10. The process of claim 1, wherein the second reaction mixture comprises ethanol, water, ethyl acetate, acetic acid, and from less than 1 wt. % acetaldehyde.

11. The process of claim 1, wherein the first reaction mixture comprises ethanol, water, ethyl acetate, acetic acid, and from 0.01 to 10 wt. % acetal.

12. The process of claim 1, wherein the first reaction mixture comprises ethanol, water, ethyl acetate, acetic acid, and from 0.01 to 10 wt. % acetaldehyde.

13. The process of claim 1, wherein less than 50% of the acetic acid in the first reaction mixture is converted in the second reaction zone.

14. The process of claim 1, wherein the first reaction mixture is fed to the second reaction zone at a gas hourly space velocity from 1500 $hr^{-1}$ to 8000 $hr^{-1}$.

15. A process for producing ethanol comprising:
feeding ethyl acetate, acetic acid, or a mixture thereof to a reactor vessel comprising the first reaction zone and second reaction zone;
hydrogenating the ethyl acetate, the acetic acid, or the mixture thereof in the first reaction zone operated at a first temperature to form a first reaction mixture comprising ethanol and one or more impurities selected from the group consisting of ethyl acetate, acetaldehyde, acetals, and mixtures thereof;
feeding a first reaction mixture to the second reaction zone, without separation; and
hydrogenating at least a portion of the one or more impurities in the second reaction zone operated at a second temperature from 50° C. to 225° C., wherein the second temperature is less than the first temperature, to form a second reaction mixture; and
recovering ethanol from the second reaction mixture, wherein the second reaction mixture comprises at least 50% less acetals than the first reaction mixture, at least 50% less acetaldehyde than the first reaction mixture, or at least 5% less ethyl acetate than the first reaction mixture.

16. The process of claim 15, wherein the first temperature is from 125° C. to 350° C.

17. A process for producing ethanol comprising:
feeding ethyl acetate, acetic acid, or a mixture thereof to a reactor vessel comprising the first reaction zone and second reaction zone;
hydrogenating the ethyl acetate, the acetic acid, or the mixture thereof in the first reaction zone first reaction zone to form a first reaction mixture comprising ethanol and one or more impurities selected from the group consisting of ethyl acetate, acetaldehyde, and acetal;
feeding a first reaction mixture to a second reaction zone, without separation; and
hydrogenating at least one of the one or more impurities in the second reaction zone to form a second reaction mixture, wherein the second reaction mixture comprises at least 50% less acetals than the first reaction mixture, at least 50% less acetaldehyde than the first reaction mixture, or at least 5% less ethyl acetate than the first reaction mixture; and
recovering ethanol from the second reaction mixture.

18. The process of claim 17, wherein the acetals are selected from the group consisting of ethyl propyl acetal, ethyl butyl acetal, diethyl acetal, dimethyl acetal, methyl ethyl acetal, and hemiacetals and mixtures thereof.

* * * * *